United States Patent [19]
Munzenberg et al.

[11] Patent Number: 5,892,085
[45] Date of Patent: Apr. 6, 1999

[54] PROCESS FOR THE PREPARATION OF HIGH-PURITY ORGANOSILICON DISULPHANES

[75] Inventors: Jorg Munzenberg, Hanau; Werner Will, Geinhausen; Gerd Zezulka, Hanau, all of Germany

[73] Assignee: Degussa Aktiengesellschaft, Frankfurt, Germany

[21] Appl. No.: 131,745

[22] Filed: Aug. 10, 1998

[30] Foreign Application Priority Data

Aug. 8, 1997 [DE] Germany ......................... 197 34 295.7

[51] Int. Cl.⁶ ....................................................... C09F 7/08
[52] U.S. Cl. ................................................................ 552/427
[58] Field of Search ................................................ 556/427

[56] References Cited

U.S. PATENT DOCUMENTS

| 4,507,490 | 3/1985 | Panster et al. | 556/427 |
| 5,596,116 | 1/1997 | Childress et al. | 556/427 |
| 5,663,395 | 9/1997 | Gobel et al. | 556/427 |
| 5,663,396 | 9/1997 | Musleve et al. | 556/427 |
| 5,770,754 | 6/1998 | Schull | 556/427 |

*Primary Examiner*—Paul F. Shaver
*Attorney, Agent, or Firm*—Pillsbury Madison & Sutro LLP

[57] ABSTRACT

The preparation of high-purity organosilicon disulphanes in which, in a two-stage process, elemental sulphur and an anhydrous alkali sulphide in a deficient amount is first reacted with a halogen alkylalkoxysilane, and the sulphur deficit is then made up by the addition of further alkali sulphide.

9 Claims, No Drawings

PROCESS FOR THE PREPARATION OF HIGH-PURITY ORGANOSILICON DISULPHANES

FIELD OF THE INVENTION

The invention relates to the preparation of high-purity organosilicon disulphanes.

BACKGROUND OF THE INVENTION

Processes for the preparation of oligosulphanes as such have been known for a long time.

In DE-PS 2141159 (U.S. Pat. No. 3,842,111), a process is described for the preparation of bis(alkoxysilylalkyl) oligosulphanes from the corresponding halogen alkylalkoxysilane and alkali metal oligosulphides, preferably in alcoholic solution. However, only mixtures of sulphanes with different chain lengths are obtained in this way.

According to a process described in DE-PS 2712866 (U.S. Pat. No. 4,129,585), an alkali metal alcoholate is reacted with a halogen alkylalkoxysilane, metal or ammonium hydrogen sulphide and sulphur in the presence of an organic solvent. The preparation of the alkali metal alcoholate solution is very time-consuming, however, which makes industrial-scale implementation of the process unlikely.

A process is known from U.S. Pat. No. 5,466,848 in which hydrogen sulphide is reacted with an alkoxide, the reaction product is treated with elemental sulphur, and then reacted with a halogen alkylalkoxysilane to obtain the desired organosilicon polysulphane.

Similarly, according to U.S. Pat. No. 5,489,701, operations are carried out with alkoxides and hydrogen sulphide, a compound which is known to be very unpleasant to handle. The reaction of anhydrous sodium sulphide and sulphur with halogen alkoxysilanes is described in the specification of JP 7-228588.

A mixture of polysulphanes is obtained in this way, as tests showed.

Organosilicon polysulphanes, particularly bis(triethoxysilylpropyl)tetrasulphane in combination with highly reactive silica fillers, are used in the preparation of vulcanised rubber articles, particularly tires.

The advantageous use of high-purity disulphanes with regard to the processing and properties of vulcanizates is described in EP-A 0732 362 (U.S. Pat. No. 5,580,919) and in Panzer (L. Panzer, American Chem. Soc., Rubber Div. Meeting 1997).

SUMMARY OF THE INVENTION

An object of the invention is to provide an advantageous process for the preparation of pure disulphanes. The attribute of "purity" relates in particular to the content of further oligo-sulphanes and monosulphanes with a different sulphur content.

The invention relates to a process for the preparation of high-purity organosilicon disulphanes corresponding to the general formula Z-Alk-S$_2$-Alk-Z (I)

in which Z represents groups

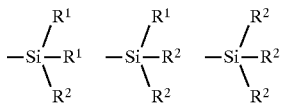

in which R$^1$ represents a linear or branched alkyl group with 1–5 carbon atoms, a cycloalkyl radical with 5–8 atoms, a benzyl radical, or the phenyl radical optionally substituted by methyl, ethyl or chlorine, R$^2$ represents for an alkoxy group with a linear or branched carbon chain with 1–5 carbon atoms or a cycloalkoxy group with 5–8 carbon atoms, a phenoxy group or a benzyloxy group, where R$^1$ and R$^2$ may in each case have the same or different meanings; and Alk represents a divalent saturated linear or branched hydrocarbon radical with 1–10 carbon atoms or the group

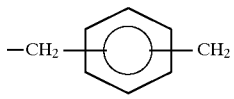

in a two-stage reaction, characterized in that
1. elemental sulphur and an anhydrous sulphide corresponding to the general formula Me$_2$S (II), in which Me represents an alkali metal or an equivalent of an alkaline earth metal atom or of zinc, or ammonium, is dissolved or suspended partially or wholly in a polar organic solvent in a molar ratio of 1:0.2 to 1:0.9, particularly 1:0.4 to 1:0.6, this solution or suspension is reacted with an organosilicon compound corresponding to the general formula Z-Alk-Hal (III)

in which Z and Alk have the meanings given above, and Hal is a chlorine or bromine atom, the molar ratio of compound (III) to sulphur (elemental) ranging from 1.2:1 to 2:1, particularly 2:1.1 to 2:1.2; and
2. after the reaction, further anhydrous Me$_2$S is added in a quantity such that the total amounts of sulphide and elemental sulphur caused to react are approximately equimolar, and the desired disulphane according to formula (I) is isolated.

To this end, the precipitated halide is filtered and the solvent is separated by distillation.

In the overall balance, the molar quantities of sulphur: compound(III): compound (II) correspond to a ratio of 1:2:1 to 1.4:2:1.4.

The starting substances according to formula (III) may be prepared according to known processes and are generally available.

In principle, the organic solvents that may be used are all polar substances in which the sulphide according to formula (II) is at least partially soluble, and which do not react with the organosilicon compound according to formula (III).

The organic solvent used is preferably a linear or ibranched alcohol with 1–5 carbon atoms, such as, e.g., methyl, ethyl, propyl, butyl or pentyl alcohol. Cycloalkylalcohols with 5–8 carbon atoms, phenol or benzyl alcohol are also suitable. Advantageously, in order to avoid, e.g.

transesterification, the alcohol corresponding in each case to the $R^2$ group is used. Optionally, the use of a mixture of these alcohols may also be advantageous, e.g. if alcohols are used. Optionally, the use of a mixture of these alcohols may also be advantageous, e.g., if $R^2$ in a compound has different meanings.

Sodium sulphide or potassium sulphide are preferably used when carrying out the process according to the invention.

In order to carry out the reaction according to the invention, it is immaterial in which form the elemental sulphur is introduced into the reactor. It is possible, with the same reaction success, to add the sulphur in solid form, e.g. as a commercial sulphur powder or granular product., or in the molten form to the $Na_2S$ solution or suspension. In order to accelerate the course of the reaction, it is expedient to use sulphur in the finely divided form, e.g. as a finely ground sulphur powder or a melt atomized into fine drops. The $Me_2S$ may be used without influencing the success of the reaction, both as a ground powder or in the form of platelets, or in the case of commercial $Me_2S$, as hydrates.

The desired anhydrous $Me_2S$ may be prepared advantageously according to the process described in DE-P 196 51849.

In formulae (I) and (III), Alk represents a divalent alkylene radical, e.g. methylene or preferably ethylene, i-propylene, n-propylene, i-butylene or n-butylene; it may also represent n-pentylene, 2-methylbutylene or 3-methylbutylene. 1,3-dimethylpropylene and 2,3-dimethylpropylene. n-Propylene is particularly suitable.

It is also recommended that the reaction be carried out with the exclusion of air and water in order to prevent the formation of by-products. It may be advantageous to carry out the reaction under reduced pressure; slightly elevated pressure is also not excluded.

A high-purity disulphane is obtained using the process according to the invention, the purity of which is markedly higher than the value of at least 80% required according to EP-A 0 732 362 for use in rubber reinforced with silica, and which, without a further purification stage, is also markedly superior to the products prepared according to the prior art in terms of the disulphide content.

DETAILED DESCRIPTION OF THE INVENTION

COMPARATIVE EXAMPLE
(Prior art)

Under inert gas, 468.25 g (6 mol) of sodium sulphide and 192.38 g (6 mol) of sulphur in 2400 ml of ethanol are charged to a 10 l three-necked flask with reflux condenser, stirrer and dropping funnel. The mixture is heated to 50° C. 2408.05 g (10 mol) of 3-chloropropyltriethoxysilane are added dropwise at such a rapid rate that the reaction can only just be controlled. (Period of dropwise addition: 25 min). After the addition has been completed, the mixture is stirred for another 2.5 h under reflux and a sample is then taken from the resulting product mixture. This sample is filtered and the solvent is removed from the filtrate. After renewed filtration, the polysulphane distribution of the filtrate is determined by $^1$H-NMR spectroscopy. According to this determination, 10.8 wt. % of monosulphane ($\delta$ 2.52 ppm), 82.8 wt. % of disulphane ($\delta$ 2.70 ppm) and 6.5 wt. % of trisulphane ($\delta$ 2.90 ppm) are present.

Examples 1–3
(according to the invention)

Example 1

Under inert gas, 234.12 g (3 mol) of sodium sulphide and 192.38 g (6 mol) of sulphur in 2400 ml of ethanol are charged to the apparatus described above for the comparative example. The mixture is heated to 50° C. 2408.05 g (10 mol) of 3-chloropropyltriethoxysilane are added dropwise in such a way that the reaction takes place in a controllable manner. (Period of dropwise addition: 12 min). The remaining sodium sulphide is then added in 4 portions of 58.53 g (0.75 mol) at 10 minute intervals. After the addition has been completed, the mixture is stirred for another 2.5 h under reflux, and a sample is taken from the resulting product mixture. This sample is filtered and the solvent removed from the filtrate. After renewed filtration, the polysulphane distribution of the filtrate is determined by $^1$H-NMR spectroscopy. According to this determination, 2.2 wt. % of monosulphane ($\delta$ 2.52 ppm) and 97.8 wt. % of disulphane ($\delta$ 2.70 ppm) are present.

Example 2
(Use of molten sulphur)

146.0 g (1.87 mol) of $Na_2S$ in 1500 ml of ethanol are charged to a 4 liter double jacket vessel with stirrer, reflux condenser and heated metering lance with nozzle. At about 30° C., 120 g (3.74 mol) of molten sulphur are sprayed into this suspension. The resulting deep yellow suspension is heated to 67° C. and 1500 g (6.23 mol) of 3-chloropropyltriethoxysilane are then metered in within 17 min. A further 146.0 g (1.87 mol) of $Na_2S$ are added to the reaction mixture in four equal portions at 10 minute intervals. After the last addition, the mixture is stirred for another 2.5 h under reflux. After cooling, a sample is taken from the resulting reaction mixture, filtered and the solvent is removed from the filtrate by evaporation. After renewed filtration, the polysulphane distribution is determined by $^1$H-NMR spectroscopy. According to this determination, 1.9 wt. % of monosulphane ($\delta$ 2.52 ppm) and 98.1 wt. % of disulphane ($\delta$ 2.70 ppm) are present.

Example 3
(Use of granulated sulphur)

A suspension of 46.83 g (0.6 mol) of $Na_2S$ in 480 ml of ethanol is charged to an apparatus corresponding to that of Example 1. 38.48 g (1.2 mol) of elemental sulphur are then added, the mixture is heated to 60° C. and 481.61 g (2 mol) of 3-chloropropyltriethoxysilane are then metered in within 4 min. A further 46.83 g (0.6 mol) of $Na_2S$ are introduced in four equal portions at 10 minute intervals. After the addition has been completed, the mixture is stirred for 2.5 h under reflux. After cooling, a sample is taken from the resulting reaction mixture, filtered, and the solvent evaporated off from the filtrate. After renewed filtration, the following polysulphane distribution is found: 2.7 wt. % of monosulphane ($\delta$ 2.52 ppm), 97.1 wt. % of disulphane ($\delta$ 2.70 ppm), 0.2 wt. % of trisulphane ($\delta$ 2.9 ppm).

What is claimed is:

1. A process for the preparation of high-purity organosilicon disulphanes corresponding to the general formula

in which Z represents groups

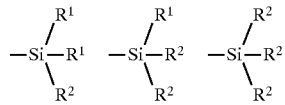

in which $R^1$ represents a linear or branched alkyl group with 1–5 carbon atoms, a cycloalkyl radical with 5–8 carbon atoms, a benzyl radical, or a phenyl radical optionally substituted by methyl, ethyl or chlorine;

$R^2$ represents an alkoxy group with a linear or branched carbon chain with 1–5 carbon atoms or a cycloalkoxy group with 5–8 carbon atoms, a phenoxy group or a benzyloxy group;

where $R^1$ and $R^2$ may in each case have the same or different meanings; and

Alk represents a divalent saturated linear or branched hydrocarbon radical with 1–10 carbon atoms or the group

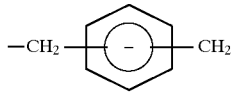

in a two-stage reaction, comprising:

A. dissolving or suspending, partially or wholly in a polar organic solvent in a molar ratio of 1:0.2 to 1:0.9, elemental sulphur and an anhydrous sulphide corresponding to the general formula

in which Me represents an alkali metal or an equivalent of an alkaline earth metal atom or of zinc, or ammonium, wherein said solution or suspension is reached with an organosilicon compound corresponding to the general formula

in which Z and Alk have the meanings given above, and Hal is a chlorine or bromine atom, the molar ratio of compound (III) to sulphur ranging from 1.2:1 to 2:1; and B. subsequently, adding further anhydrous $Me_2S$ in a quantity such that the total amount of sulphide and elemental sulphur caused to react are approximately equimolar, and the desired disulphane is isolated.

2. A process according to claim 1, comprising using alcohols of aromatic hydroxy compounds corresponding in each case with radical $R^2$ as solvent.

3. A process according to claim 1, wherein the sulphide comprises sodium sulphide or potassium sulphide.

4. A process according to claim 1, comprising:

dissolving or suspending the elemental sulphur and the sulphide according to formula (II) in a molar ratio of 1:0.4 to 1:0.6 in step A.

5. A process according to claim 1, comprising:

using the compounds (II), (III) and sulphur in molar quailities that correspond to a total balance of sulphur: compound III: compound II of 1:2:1 to 1.4:2:1.4.

6. A process according to claim 1, wherein the organosilicon compound according to formula (II) used is 3-chloropropyltriethoxysilane or methoxysilane.

7. A process according to claim 1, wherein the sulphur is used in the form of a finely atomised melt.

8. A process according to claim 1, wherein the sulphur is used as a finely ground powder.

9. A process according to claim 1, comprising adding the anhydrous $Me_2S$ in partial amounts in step B.

* * * * *